United States Patent
Leigh et al.

(10) Patent No.: US 10,792,504 B2
(45) Date of Patent: Oct. 6, 2020

(54) MALLEABLE IMPLANTABLE MEDICAL DEVICE

(71) Applicant: COCHLEAR LIMITED, Macquarie University (AU)

(72) Inventors: Charles R. A. Leigh, East Ryde (AU); Evelia Ysabel Medina-Taylor, Davidson (AU)

(73) Assignee: COCHLEAR LIMITED, Macquarie University (AU)

( * ) Notice: Subject to any disclaimer, the term of this patent is extended or adjusted under 35 U.S.C. 154(b) by 794 days.

(21) Appl. No.: 15/143,199

(22) Filed: Apr. 29, 2016

(65) Prior Publication Data

US 2016/0235988 A1    Aug. 18, 2016

Related U.S. Application Data

(62) Division of application No. 14/338,920, filed on Jul. 23, 2014, now Pat. No. 9,731,128, which is a division of application No. 12/036,110, filed on Feb. 22, 2008, now abandoned.

(51) Int. Cl.

| | |
|---|---|
| *A61N 1/378* | (2006.01) |
| *A61N 1/375* | (2006.01) |
| *A61N 1/36* | (2006.01) |
| *A61N 1/05* | (2006.01) |
| *A61N 1/372* | (2006.01) |
| *A61F 11/00* | (2006.01) |
| *A61F 2/30* | (2006.01) |

(52) U.S. Cl.
CPC ......... *A61N 1/3787* (2013.01); *A61N 1/0541* (2013.01); *A61N 1/36036* (2017.08); *A61N 1/375* (2013.01); *A61N 1/37223* (2013.01); *A61F 11/004* (2013.01); *A61F 2002/30583* (2013.01); *A61F 2210/0085* (2013.01); *H04R 2225/67* (2013.01)

(58) Field of Classification Search
CPC .............. A61N 1/36032; A61N 1/0541; A61N 1/37223; A61N 1/375; A61N 1/3787; A61F 11/004; A61F 2210/0085; H04R 2225/67
See application file for complete search history.

(56) References Cited

U.S. PATENT DOCUMENTS

| | | | |
|---|---|---|---|
| 8,457,753 B2 * | 6/2013 | Greenberg | ......... A61N 1/36046 607/53 |
| 2002/0019669 A1 * | 2/2002 | Berrang | ............. A61N 1/36036 623/10 |
| 2004/0078004 A1 * | 4/2004 | Bourne | ................. A61M 39/04 604/174 |
| 2004/0173221 A1 | 9/2004 | Singhal et al. | |
| 2004/0176814 A1 | 9/2004 | Singhal et al. | |
| 2004/0260361 A1 | 12/2004 | Gibson | |
| 2005/0159791 A1 | 7/2005 | Daly et al. | |

(Continued)

*Primary Examiner* — Lindsey G Wehrheim
(74) *Attorney, Agent, or Firm* — Merchant & Gould P.C.

(57) ABSTRACT

A malleable implantable medical device for implanting in a recipient comprising a flexible region of the medical device, one or more structures proximate to the flexible region, wherein the one or more structures is configured to provide a bending force to the flexible region, and one or more hermetically sealed medical components coupled to the flexible region, wherein the one or more medical components is configured to provide a therapeutic effect on the recipient.

20 Claims, 11 Drawing Sheets

(56) References Cited

U.S. PATENT DOCUMENTS

2006/0247734 A1* 11/2006 Greenberg ........... A61N 1/0543
607/54
2007/0073128 A1    3/2007 Hoarau et al.

* cited by examiner

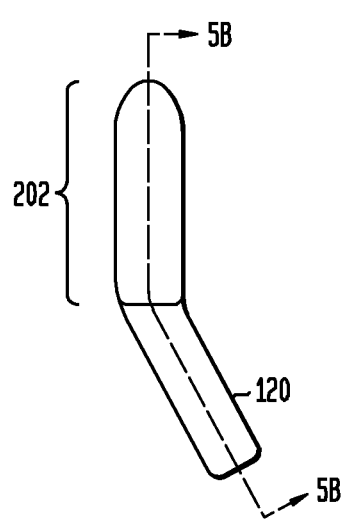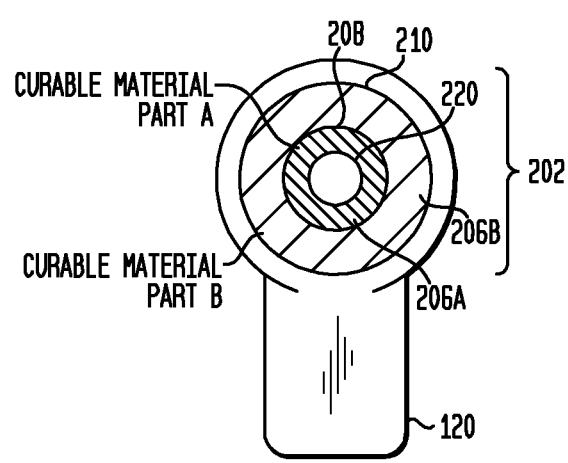

FIG. 12
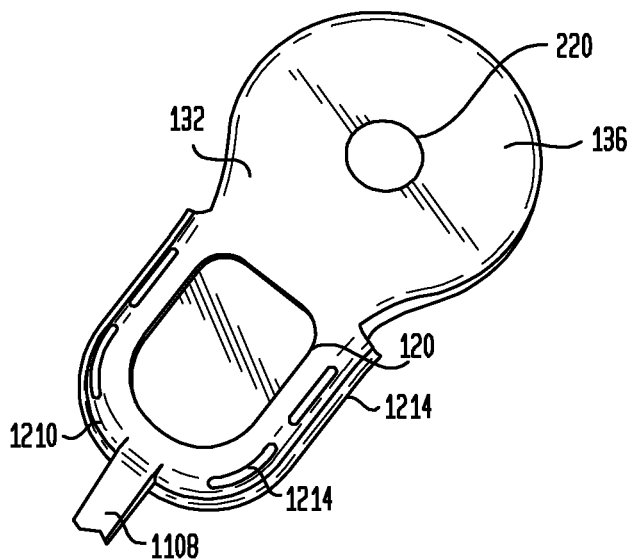
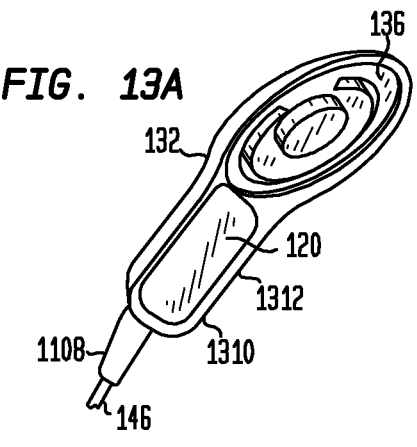
FIG. 13A
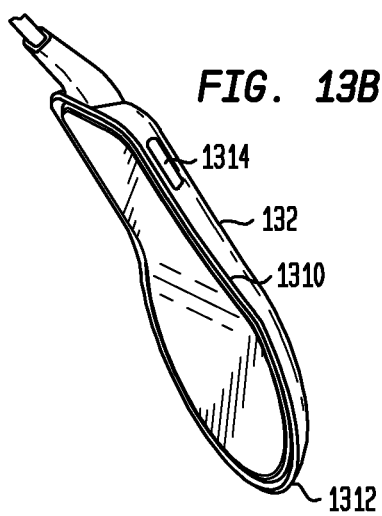
FIG. 13B

MALLEABLE IMPLANTABLE MEDICAL DEVICE

CROSS-REFERENCE TO RELATED APPLICATIONS

The present application is a divisional of U.S. patent application Ser. No. 14/338,920, filed on Jul. 23, 2014, entitled "MALLEABLE IMPLANTABLE MEDICAL DEVICE", now U.S. Pat. No. 9,731,128, which is a divisional of U.S. patent application Ser. No. 12/036,110, filed on Feb. 22, 2008, entitled "MALLEABLE IMPLANTABLE MEDICAL DEVICE"; the disclosures of which are hereby incorporated by reference herein.

BACKGROUND

Field of the Invention

The present invention relates generally to implantable medical devices, and more particularly, to malleable implantable medical devices.

Related Art

Implantable medical devices have been used to provide therapeutic benefits to patients for a host of reasons. For example, implantable medical devices may provide therapeutic benefits for those patients who have experienced hearing loss by enhancing or replacing hearing stimulation which they are no longer able to experience. Hearing loss, which may be due to many different causes, is generally of two types, conductive and sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often addressed with conventional hearing aids which amplify sound.

Many people who are profoundly deaf, however, have sensorineural hearing loss. This type of hearing loss is due to the absence or destruction of the hair cells in the cochlea which transduce acoustic signals into nerve impulses. Those suffering from sensorineural hearing loss are thus unable to derive suitable benefit from conventional hearing aids due to the damage to or absence of the mechanism for naturally generating nerve impulses in response to sound.

It is for this purpose that another type of auditory prosthesis, a cochlear implant (also commonly referred to as cochlear prostheses, cochlear devices, cochlear implant devices, and the like; generally and collectively referred to herein as "cochlear implants") has been developed. Stimulating auditory prostheses such as cochlear implants bypass the hair cells in the cochlea, directly delivering electrical stimulation to the auditory nerve fibers via an implanted electrode assembly. This enables the brain to perceive a hearing sensation resembling the natural hearing sensation normally delivered to the auditory nerve.

Certain implantable medical devices such as cochlear implants are positioned directly underneath the skin and/or placed into an excavated portion of the recipient's bone or tissue. Other implantable medical devices are placed directly on the bone without excavation. A portion of the implanted devices may extend away from the bone or may extend outward from the bone or excavated portion.

SUMMARY

Embodiments of the present invention are generally directed to a malleable implantable medical device which is configurable to conform to the shape of a patient's bone, skull or other natural or artificial structure found at the implantation site. In some embodiments, the malleable implantable medical device comprises one or more therapeutic or medical components, a flexible portion of the device coupled to the therapeutic or medical components, and a structure which is configured to provide a bending force to the flexible portion such that the implantable medical device conforms to a desired shape, such as to the curvature of the recipient's bone or skull. In other embodiments, the malleable implantable medical device may be position in or around the patient's bone, skull or other natural or artificial structures found at the implantation site such that one or more of those structures provide a bending force to the flexible portion of the device in order to have the flexible portion conform to the structure at the implantation site. In yet other embodiments, portions of the malleable implantable medical device are optionally removable in order to have the medical device conform to the shape of a patient's bone, skull or other natural or artificial structures found at the implantation site.

In one embodiment of the present invention, a malleable implantable medical device for implanting in a recipient is provided comprising a flexible region of the medical device, one or more structures proximate to the flexible region, wherein the one or more structures is configured to provide a bending force to the flexible region, and one or more hermetically sealed medical components coupled to the flexible region, wherein the one or more medical components is configured to provide a therapeutic effect on the recipient.

BRIEF DESCRIPTION OF THE DRAWINGS

Embodiments of the present invention are described below with reference to the attached drawings, in which:

FIG. 5A is a side view of a malleable implantable medical device in accordance with one embodiment of the present invention;

FIG. 5B is a cross-sectional view of the malleable implantable medical device of FIG. 5A in accordance with one embodiment of the present invention;

FIG. 12 is a perspective view of a flexible wing proximate to an internal coil of a malleable implantable medical device in accordance with an embodiment of the present invention;

FIG. 13A is a perspective bottom view of a flexible wing proximate to both a stimulator unit and an internal coil of a malleable implantable medical device in accordance with an embodiment of the present invention;

FIG. 13B is a perspective bottom view of a flexible wing proximate to both a stimulator unit and an internal coil of a malleable implantable medical device in accordance with another embodiment of the present invention;

DETAILED DESCRIPTION

Embodiments of the present invention are generally directed to a malleable implantable medical device which can be configured to conform to the shape of a patient's bone, skull or other natural or artificial structures found at the implantation site. In some embodiments, the malleable implantable medical device comprises one or more therapeutic or medical components, a flexible portion of the device which is coupled to the therapeutic or medical components, and a structure which is configured to provide a bending force to the flexible portion such that the implantable medical device conforms to a desired shape, such as to the curvature of the recipient's bone or skull. In other embodiments, the malleable implantable medical device may be position in or around the patient's bone, skull or other natural or artificial structures found at the implantation site such that one or more of those structures provide a bending force to the flexible portion of the device in order to have the flexible portion conform to the structure at the implantation site. In yet other embodiments, portions of the malleable implantable medical device are optionally removable in order to have the medical device conform to the shape of a patient's bone, skull or other natural or artificial structures found at the implantation site.

The malleable implantable medical device of the present invention will be described in conjunction with an implanted unit of a prosthetic hearing implant, such as a Cochlear™ implant sold by Cochlear Limited. It should be understood to those skilled in the art that the present invention may be used in other implanted medical devices, such as neuro-stimulators, cardiac pacemakers/defibrillators, etc.

Figure 1:
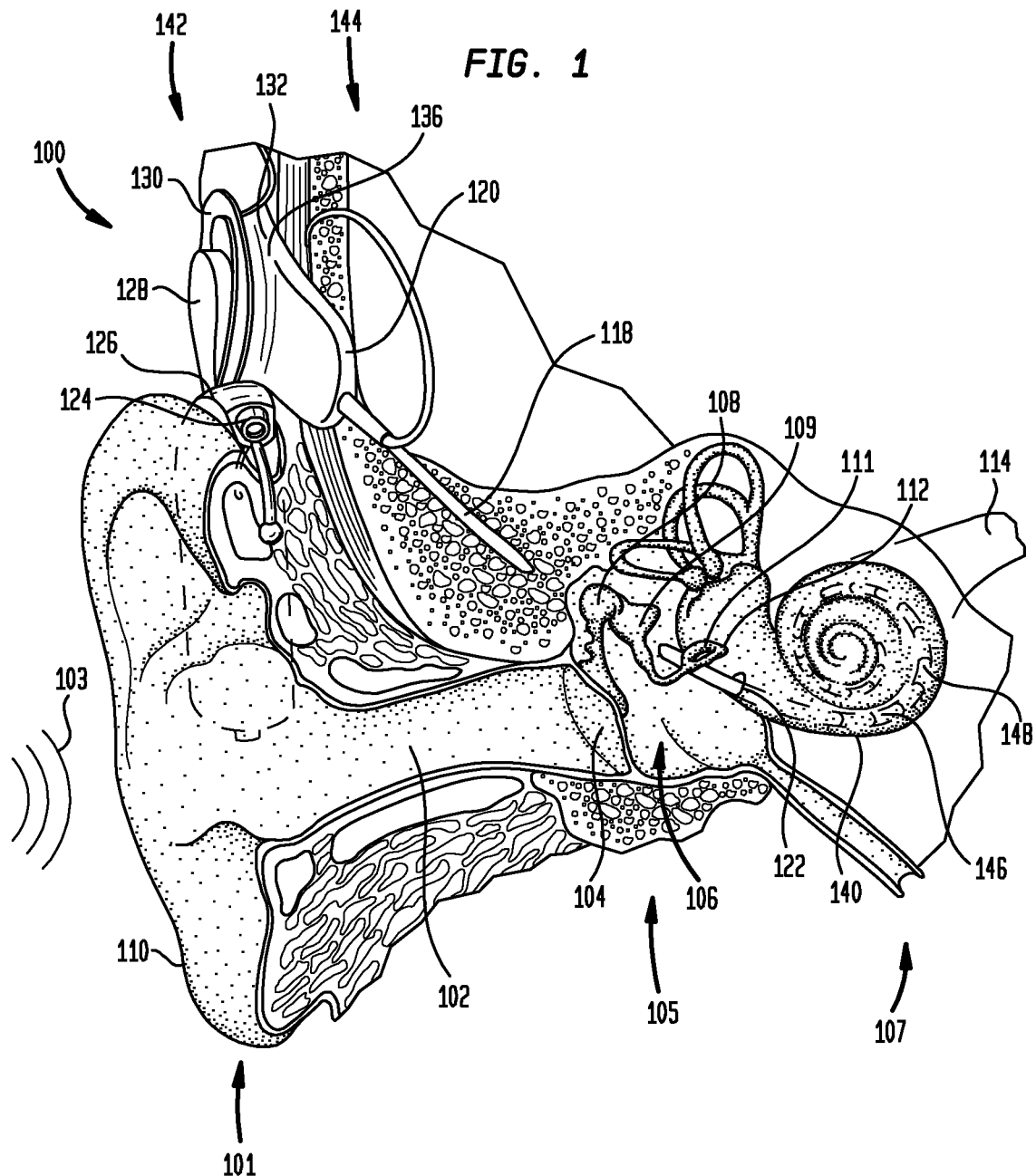
FIG. 1 is a perspective view of a malleable implantable medical device in accordance with one embodiment of the present invention.

FIG. 1 is perspective view of one embodiment of a cochlear implant 100 implanted in a human cochlea 140. Referring now to FIG. 1, the relevant components of outer ear 101, middle ear 105 and inner ear 107 are described next below. In a fully functional ear outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate. Such vibration sets up waves of fluid motion within cochlea 140. Such fluid motion, in turn, activates tiny hair cells (not shown) that line the inside of cochlea 140. Activation of the hair cells causes appropriate nerve impulses to be transferred through the spiral ganglion cells and auditory nerve 114 to the brain, where they are perceived as sound.

Cochlear implant 100 comprises external component assembly 142 which is directly or indirectly attached to the body of the recipient, and an internal component assembly 144 which is temporarily or permanently implanted in the recipient. External assembly 142 typically comprises microphone 124 for detecting sound, a speech processing unit 126, a power source (not shown), and an external transmitter unit 128. External transmitter unit 128 comprises an external coil 130 and, preferably, a magnet (not shown) secured directly or indirectly to external coil 130. Speech processing unit 126 processes the output of microphone 124 that is positioned, in the depicted embodiment, by auricle 110 of the recipient. Speech processing unit 126 generates coded signals, referred to herein as a stimulation data signals, which are provided to external transmitter unit 128 via a cable (not shown).

Internal assembly 144 comprises an internal receiver unit 132, a stimulator unit 120, and an elongate electrode carrier 118. Internal receiver unit 132 comprises an internal coil 136, and preferably, a magnet (also not shown) fixed relative to internal coil 136. Internal receiver unit 132 and stimulator unit 120 are hermetically sealed within a biocompatible housing. The internal and external coils form a transcutaneous link such that the internal coil receives power and stimulation data from external coil 130. Elongate electrode carrier 118 has a proximal end connected to stimulator unit 120 and extends from stimulator unit 120 to cochlea 140. Elongate electrode carrier 118 is implanted into cochlea 140 via a cochleostomy 122.

Elongate electrode carrier 118 comprises an electrode array 146 disposed at the distal end thereof. Electrode array 146 comprises a plurality of longitudinally-aligned electrodes 148. Stimulation signals generated by stimulator unit 120 are applied by electrodes 148 to cochlea 140, thereby stimulating auditory nerve 114.

External coil 130 transmits electrical signals (i.e., power and stimulation data) to the internal coil 136 via a radio frequency (RF) link. The internal coil 136 is typically comprised of multiple turns of electrically insulated single-strand or multi-strand platinum or gold wire. The electrical insulation of the internal coil 136 is provided by a flexible silicone molding (not shown). In use, implantable internal receiver unit 132 may be positioned in a recess of the temporal bone (not shown) adjacent auricle 110 of the recipient.

Figure 2A:
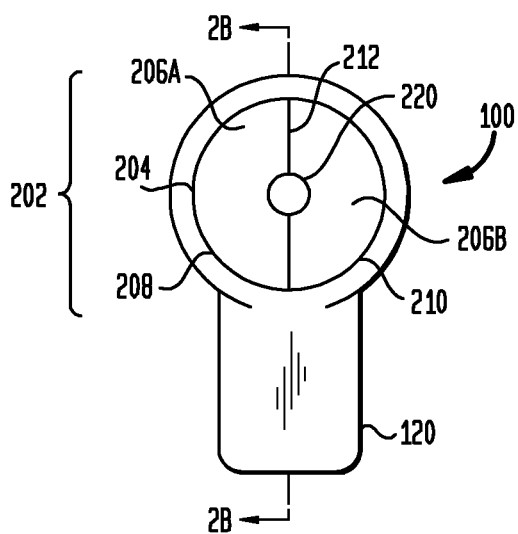
FIG. 2A is a top view of a malleable implantable medical device in accordance with one embodiment of the present invention.

FIG. 2A is a top view of a cochlear implant 100 in accordance with one embodiment of the present invention. As discussed previously, cochlear implant 100 comprises an internal receiver unit 132 having an internal coil 136 and is hermetically sealed in biocompatible housing. The portion of the housing for internal receiver unit 132 having internal coil 136 may be made of a flexible elastomer (e.g. silicone) such that it will bend when a bending force is applied to the housing. In one embodiment of the present invention, this portion, referred to as flexible region 202, contains a sealed chamber 204 with one or more curable materials 206 contained within chamber 204. The one or more curable materials 206 contained therein may be cured or otherwise activated, as will be discussed further below. By curing curable materials 206 inside of a flexible region 202 of the implantable medical device, flexible region 202 adopts and retains the shape into which curable materials 206 are cured. For purposes of this invention, "curable" material should be understood to include materials that can be cured with the application of just energy, such as heat or UV-light, without the addition or other chemicals, compounds or other materials. It should also be understood that "curable" material includes materials which, though not capable of being cured or otherwise activated by itself or even with the addition of various energies such as heat or UV-light, are capable of curing or activating upon the addition of an added chemical, compound or material, either with and without additional energy (e.g., heat, UV-light) being applied to a mixture of the first and second "curable" materials. Curable material 206 may be a curable silicone elastomer, but may also be any other material suitable for use according to the present invention.

Figure 2B:
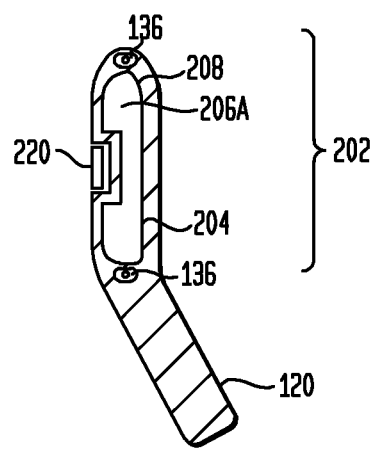
FIG. 2B is a cross-sectional view of the malleable implantable medical device of FIG. 2A in accordance with one embodiment of the present invention.

In other embodiments of the present invention, chamber 204 may be divided into two or more sub-chambers, with different curable materials contained in each sub-chamber. As depicted in FIGS. 2A and 2B, in an exemplary embodiment, first sub-chamber 208 may contain a first curable material and second sub-chamber 210 may contain a second curable material, with sub-chambers 208, 210 and internal magnet 220 configured and positioned such that the integrity of sub-chambers 208, 210 are maintained even with the magnet disposed on or within flexible region 202. Sub-chambers 208, 210 may be manufactured initially as a single chamber 204 with a thin dividing membrane 212 attached within chamber 204, thereby dividing chamber 204 into sub-chambers 208, 210, and attached in such a manner that the first and second curable materials placed within sub-chambers 208, 210 do not intermix until they are intentionally combined by an external force. Alternatively, sub-chambers 208, 210 may be manufactured through injection moulding, or some other process now known or later developed, to form the two sub-chambers 208, 210.

Figure 2C:
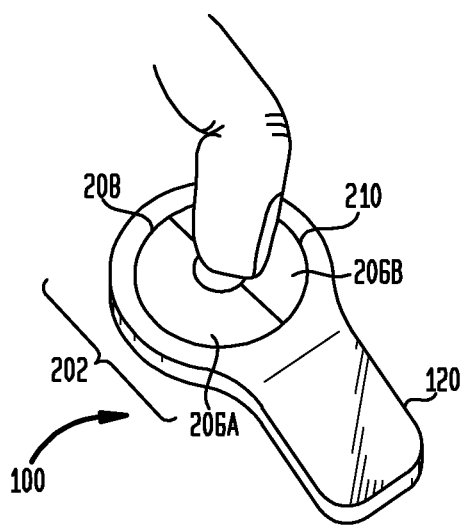
FIG. 2C is a perspective view of a malleable implantable medical device in accordance with one embodiment of the present invention as force is being manually applied to the device.

Curable materials 206 may be cured or otherwise activated so as to change its state from a liquid or gel or paste into a solid upon activation. In one exemplary embodiment wherein flexible region 202 of the cochlear implant 100 has a single chamber 204 containing a single curable material 206, an external energy such as heat or light (e.g., UV-light) may be applied in order to cure or activate curable material 206 contained therein. In another exemplary embodiment depicted in FIGS. 2A-2D, flexible region 202 of the cochlear implant 100 has two sub-chambers 208 and 210, each with two different curable materials 206 which chemically interact with one another, with or without external energy such as heat or UV-light, to change the state of curable materials 206 into a solid. In other embodiments, the two different curable materials 206 may not cure or activate even when intermixed without the addition of an external heat or light energy applied to the mixed curable materials 206. By applying manual force to flexible region 202 using one or more fingers or hands, as shown in FIG. 2C, or by using other tools, dividing membrane 212 is deformed or broken sufficiently to permit intermixing of the different curable materials 206 with each other. Curable materials 206 may be further mixed by continued massaging or pushing forces applied manually, to ensure a substantially complete intermixing of curable materials 206. Alternatively, once dividing membrane 212 is sufficiently deformed or broken to allow the intermixing of curable materials 206, curable materials 206 may naturally intermix without external forces being applied to a sufficient level so as to cause the curing or activating of curable materials 206.

Figure 2D:
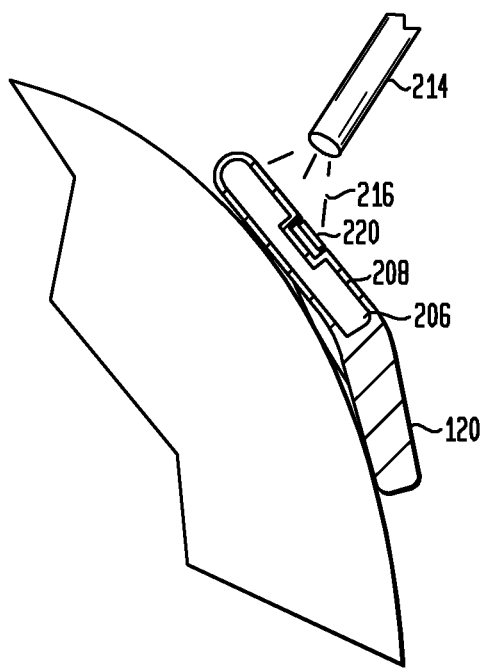
FIG. 2D is a cross-sectional view of the malleable implantable medical device of FIG. 2A in accordance with one embodiment of the present invention as an activating light is directed to the device.

As shown in FIG. 2D, after curable materials 206 are intermixed with one another so as to initiate the curing or activating process, the flexible region 202 is placed against the patient's bone, skull or other structure so that curable materials 206 cure or activate, resulting in flexible region 202 conforming to the shape of the object being pressed against. In other embodiments, as shown in FIG. 2D, UV curing light 214 emits UV light 216 in the direction of flexible region 202 to cure curable material 206 contained therein, where curable material 206 is a type which will cure only upon the addition of UV light 216. When flexible region 202 is placed against the patient's bone or skull, a bandage or other temporary holding means may be used to hold flexible region 202 in a fixed location and configuration, allowing curable materials 206 to cure or activate into a desirable shape. Alternatively, measurements of the structure to which the implantable medical device is to conform to may be taken prior to surgery and used to cure or activate curable materials 206 prior to surgery, so that the cured flexible region 202 may more accurately reflect the shape to conform to, or so that the amount of time during which the implantation site is open during surgery can be minimized, among other reasons. These measurements may be taken directly by measuring the shape of the bone or skull when accessible, or may be taken indirectly through data gathered during an x-ray, MRI, CT-scan, or other methods now known or later developed. Further these measurements may be used to create an accurate model of the area the malleable implant is to be placed using a CNC machine to cut the shape from a solid or by using a 3D printer or other method now known or later developed. Upon curing or activating, curable materials 206 may remain flexible, and may have a softness on the durometer scale (shore A) of approximately 30-60. It is to be understood that the types of curable materials selected for other embodiments of the present invention may depend on the intended uses for the implantable medical device, the techniques or tools used for implanting the medical device, among other factors.

Figure 3A:
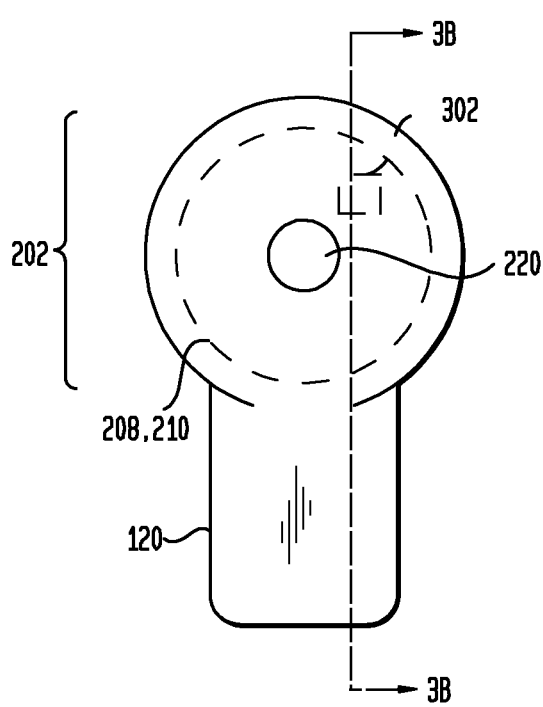
FIG. 3A is a top view of a malleable implantable medical device in accordance with one embodiment of the present invention.
Figure 3B:
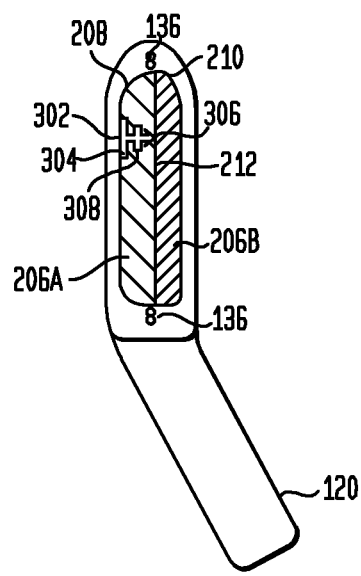
FIG. 3B is a cross-sectional view of the malleable implantable medical device of FIG. 3A in accordance with one embodiment of the present invention.

In addition to sub-chambers 208, 210 being positioned in a side-by-side configuration as shown in FIG. 2A, other embodiments of the present invention may be configured to have sub-chambers 208, 210 in a top-bottom configuration wherein the layers are positioned on top of one another, as shown in FIGS. 3A and 3B. This top-bottom configuration may permit a more complete intermixing, or a faster intermixing, of curable materials 206A, 206B. Additionally, this top-bottom configuration may permit the incorporation of punching tool 302 into sub-chamber 208. Punching tool 302 has a pushing surface 304 against which manual pressure, from a finger or another tool, can push to cause sharp tip 306 of punching tool 302 to be forced through dividing membrane 212, thus permitting the intermixing of curable material 206A and 206B. Stopper 308 may limit the depth to which punching tool 302 may travel so as not to damage the opposing wall of chamber 204, were sharp tip 306 not prevented from traveling too far. The top-bottom configuration depicted in FIGS. 6A and 6B may be preferable when incorporating punching tool 302 since even a slight pressure applied to the broad surface of flexible region 202 will push the tip of punching tool 302 through dividing membrane.

Figure 4A:
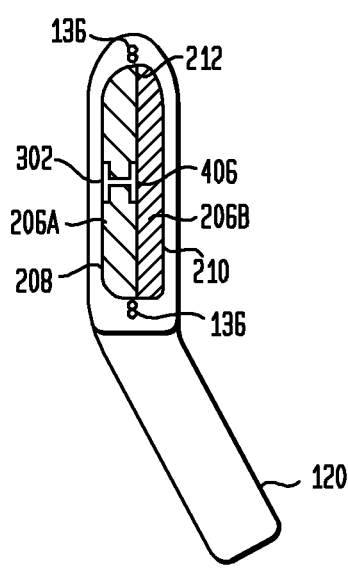
FIG. 4A is a cross-sectional view of a malleable implantable medical device in accordance with another embodiment of the present invention.
Figure 4B:
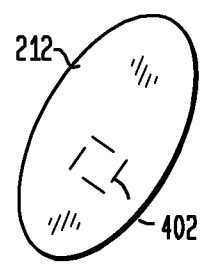
FIG. 4B is a perspective view of a thin membrane used in a malleable implantable medical device in accordance with another embodiment of the present invention.

As shown in FIGS. 4A and 4B, in other embodiments of the present invention, punching tool 302 may not have a sharp tip as in the embodiment described above in conjunction with FIG. 3B. In the embodiment shown in FIGS. 4A and 4B, punching tool 302 has pushing surface 304 and a broad or flat pushing tip 406. Dividing membrane 212 has perforated region 402 sized and configured to be pushed apart from membrane 212 by pushing tip 406 when a manual force is applied to pushing surface 304, which will provide an access for curable materials 206A and 206B to travel between first chamber 208 and 210 in order that curable materials 206A and 206B can intermix.

FIGS. 5A and 5B are side and cross-sectional views respectively of a cochlear implant 100 in accordance with one embodiment of the present invention. In the embodiment shown, first and second sub-chambers 208 and 210 are concentric with respect to one another, within dividing membrane 212 positioned between sub-chambers 208, 210. Upon manual pressure being applied to dividing membrane 212, curable materials 206A, 206B are permitted to intermix, in the manner described above.

Figure 6:
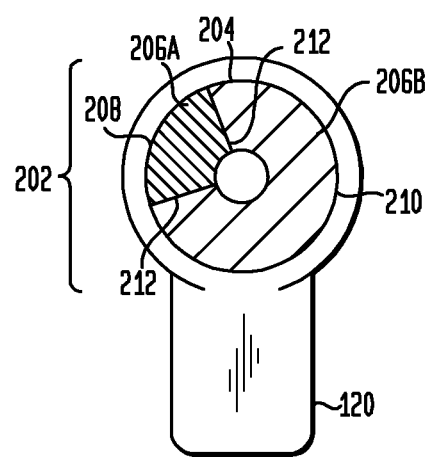
FIG. 6 is a top view of a malleable implantable medical device in accordance with one embodiment of the present invention.

Although previously described embodiments have referenced figures in which first and second sub-chambers 208, 210 appear to be equal in size, thus containing approximately equal volumes of curable materials 206A, 206B, it is to be understood that sub-chambers 208, 210 may be of different sizes, as shown in FIG. 6. Furthermore, it is to be understood that sub-chambers 208, 210 may be completely filled with curable material 206 or may only be partially filled with curable material 206 under the present invention. In FIG. 6, flexible region 202 contains chamber 204 having first sub-chamber 208 and second sub-chamber 210 which is defined by the presence of dividing membrane 212 in chamber 204 so as to define sub-chambers 208, 210. The embodiment of FIG. 6 may be useful where the volumes of curable material 206A and 206B are necessarily unequal with respect to one another to achieve a desired curing aspect such as speed or type of curing.

Figure 7:
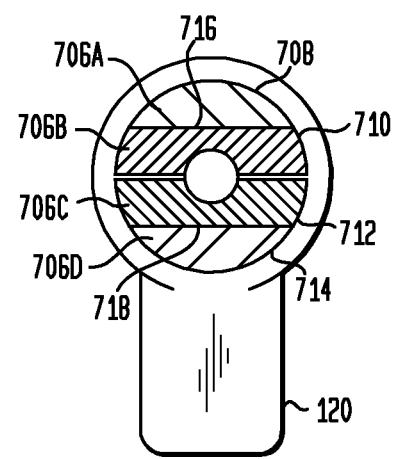
FIG. 7 is a top view of a malleable implantable medical device in accordance with one embodiment of the present invention.

It is further to be understood that, although multi-chamber configurations described previously have referred only to a first and second sub-chamber, more than two sub-chambers may be present in chamber 204 according to the present invention. In FIG. 7, in an exemplary embodiment, sub-chambers 708, 710, 712, 714 contain curable materials 706A, 706B, 706C, 706D respectively, wherein dividing membrane 716 separates sub-chambers 708, 710 and wherein dividing membrane 718 separates sub-chambers 712, 714. By having two sets of sub-chambers (708/710 and 712/714) in the embodiment of FIG. 7, a first set may be manipulated and cured prior to manipulating and curing the second set, where doing so may be desirable for accuracy or other reasons. Additionally, curable materials 706A, 706B intermixed in the first set of sub-chambers 708, 710 may be selected to provide a different result, such as a different softness or level of flexibility, than curable materials 706C, 706D intermixed in the second set of sub-chambers 712, 714.

Figure 8A:
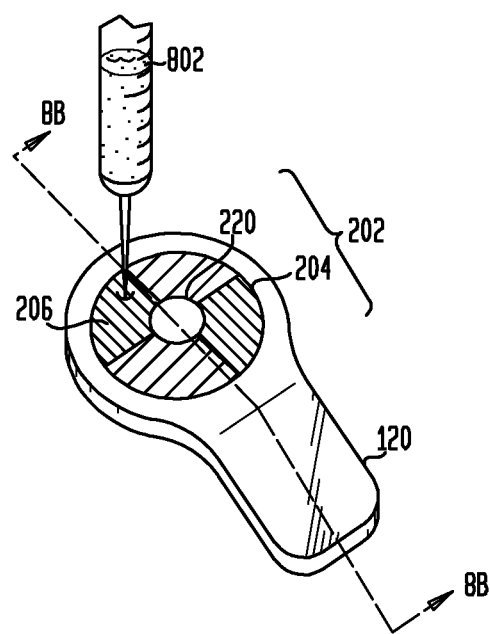
FIG. 8A is a perspective view of a malleable implantable medical device in accordance with one embodiment of the present invention.
Figure 8B:
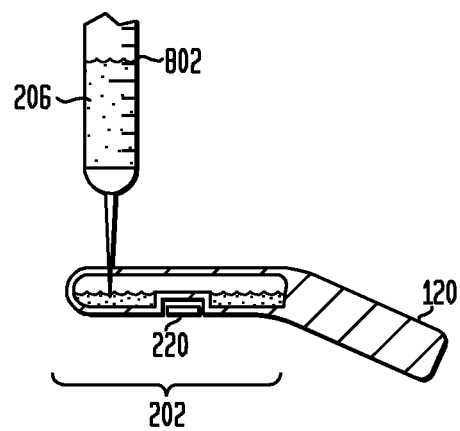
FIG. 8B is a cross-sectional view of the malleable implantable medical device of FIG. 8A in accordance with one embodiment of the present invention.

FIGS. 8A and 8B are perspective views of a cochlear implant 100 in accordance with another embodiment of the present invention. In addition to, or instead of, providing a curable material 206 in chamber 204, curable material 206 may be provided to the space defined by chamber 204 through the use of a syringe 802. Syringe 802 may be filled with curable material 206 and inserted into a surface of flexible region 202, then plunged so as to fill chamber 204 with curable material 206. Curable material 206 may be a single material which can be cured or activated without the addition of a catalyst or other material, through one or more energies (e.g., heat) or light (e.g., UV-light) being applied to curable material 206. In alternative embodiments, chamber 204 may be filled with a first curable material 206A of a multi-part curable material arrangement in which a second and necessary curable material 206B, such as a catalyst, may be provided to chamber 204 through syringe 802. In yet another embodiment of the present invention, chamber 204 may be substantially empty, whereby curable materials 206A and 206B in a self-curing or self-activating are intermixed and immediately provided to chamber 204 through syringe 802 before curable materials 206A and 206B cure or activate in a solid which provides a bending stress to flexible region 202, as described previously.

Figure 9A:
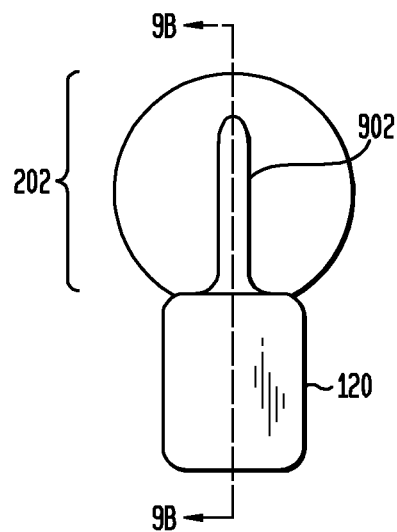
FIG. 9A is a bottom view of a malleable implantable medical device in accordance with one embodiment of the present invention.
Figure 9B:
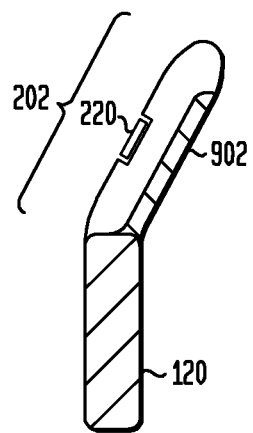
FIG. 9B is a cross-sectional view of the malleable implantable medical device of FIG. 9A depicting a condition of the device before a bending force is applied in accordance with one embodiment of the present invention.
Figure 9C:
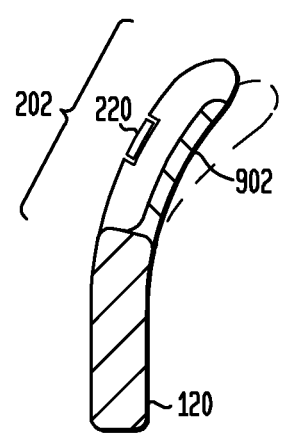
FIG. 9C is a cross-sectional view of the malleable implantable medical device of FIG. 9A depicting a condition of the device after a bending force is applied in accordance with one embodiment of the present invention.

In yet another embodiment of the present invention in which a bending force is provided to a flexible region 202 of an implantable medical device, FIGS. 9A-9C shows an embodiment in which a bendable structure 902 is provided against a surface of flexible region 202 and bent by a desired amount, resulting in the bending of flexible region 202. As shown in FIG. 9A, a bendable structure 902 is adhered to a surface of flexible region 202. As shown in FIG. 9B, in other embodiments, bendable structure 902 is embedded within silicone flexible region 202. As shown in FIG. 9C, when bendable structure 902 is bent, it retains the angle into which it was bent, and causes flexible region 202 to adopt a similar angle. Bendable structure 902 may be a metal or alloy such as titanium in some embodiments, and may be configured in the shape of a spine, but may also be a non-metallic structure such as a series of interlocking plastic structures configured to be bent and to retain the bend with sufficient force to counteract any straightening force which may be exerted by flexible region 202. In addition to bendable structure 902 being positioned on the surface of internal receiver unit 132 facing the recipient's bone or skull in certain embodiments, bendable structure 902 may be positioned along the outer or other surface of internal receiver unit in other embodiments of the present invention, depending on the intended use and other considerations. Multiple bendable structures similar to 902 may be used to create different levels of curvature in different locations which may allow still closer fit to the shape of the bone or skull or other feature.

Figure 10A:
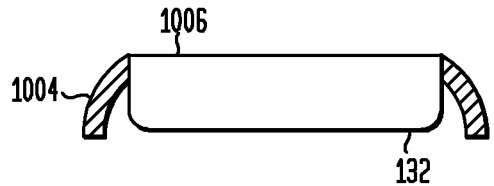
FIG. 10A is a cross-sectional view of a flexible wing proximate to a stimulator unit of a malleable implantable medical device in accordance with an embodiment of the present invention.

FIGS. 10A, 10B, 10C, 10D, 10E are cross-sectional views of a flexible wing proximate to a stimulator unit of a cochlear implant 100 in accordance with an embodiment of the present invention. Internal receiver unit 132 of a cochlear implant 100 has wing 1004 constructed in various exemplary embodiments of the present invention. Internal receiver unit 132 may be implanted into a recipient by attaching internal receiver unit 132 to a bone or tissue or inserting internal receiver unit 132 into an excavated bone. Wing 1004 is flexible and may extend around the entire perimeter or circumference of internal receiver unit 132 or a portion thereof. FIG. 10A shows wing 1004 attached near an upper surface 1006 of internal receiver unit 132. Wing 1004 may extend beyond internal receiver unit 132 so that when inserted, wing 1004 may begin to flex outward before internal receiver unit 132 rests on the bone or tissue.

Figure 10B:
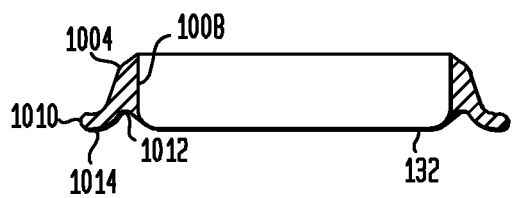
FIG. 10B is a cross-sectional view of a flexible wing proximate to a stimulator unit of a malleable implantable medical device in accordance with an embodiment of the present invention.

FIG. 10B shows wing 1004 attached along a side surface 1008 of internal receiver unit 132. Wing 1004 has a rim 1010 that contacts the bone or tissue and also has an indentation 1012 along a lower surface 1014 of wing 1004.

Figure 10C:
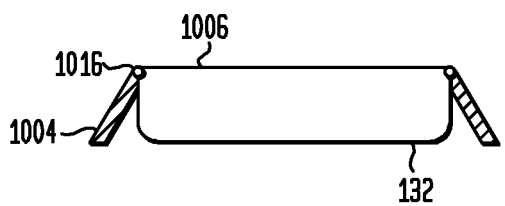
FIG. 10C is a cross-sectional view of a flexible wing proximate to a stimulator unit of a malleable implantable medical device in accordance with an embodiment of the present invention.

FIG. 10C shows wing 1004 having a hinge 1016 near upper surface 1006 of internal receiver unit 132. Hinge 1016 allows wing 1004 to pivot in addition to flexing. Wing 1004 may be adhered to hinge 1016, and hinge 1016 may be integral or adhered to internal receiver unit 132. Wing 1004 is shown with a constant slope, but may have a slope substantially similar to FIG. 10A or 10B.

Figure 10D:
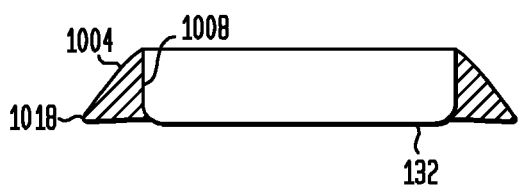
FIG. 10D is a cross-sectional view of a flexible wing proximate to a stimulator unit of a malleable implantable medical device in accordance with an embodiment of the present invention.

FIG. 10D shows wing 1004 having a solid skirt 1018 that extends along side surface 1008 of internal receiver unit 132. Solid skirt 1018 may have a rim 1010 as shown in FIG. 10B. Solid skirt 1018 may be made of a flexible material that bends and compresses.

Figure 10E:
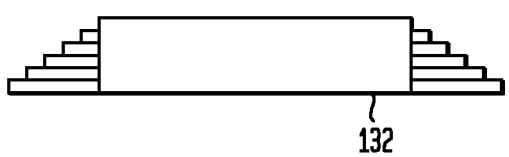
FIG. 10E is a cross-sectional view of a flexible wing proximate to a stimulator unit of a malleable implantable medical device in accordance with an embodiment of the present invention.

FIG. 10E shows wing 1004 that extends along side surface 1008 of internal receiver unit 132 and has a series of removable segments 1020. Each removable segment 1020 may be detached to accommodate the depth of the bone excavation or the position/arrangement of the bone or tissue. The portion of wing 1004 that remains intact may be flexible or may have a solid skirt 1018 as shown in FIG. 10D.

The wing cross-sections shown in FIGS. 10A, 10B, 10C, 10D, and 10E may also be integral with the hermetically sealed biocompatible housing surrounding internal receiver unit 132 of the medical device. In addition, the wing may be part of a slipcover that extends over the housing of the medical device and is held on by an adhesive and/or the friction of the slipcover.

When a medical device is inserted into a bone excavation the wing will flex outwards to form a smooth transition from the medical device to the bone. In addition, when a medical device rests on a bone or other tissue, the wing may also flex outwards to form a smooth transition. The flexing of the wing may be uniform around the perimeter or circumference of the housing or the wing may flex more along some portions and less along other portions depending on the nature of the medical device and/or the nature of the bone or tissue surrounding the medical device. Embodiments of the present invention may allow the wing to move away from the medical device when the medical device is positioned into the bone excavation. The free end of the wing, i.e., the end not adhered to the medical device, remains in contact with the bone or tissue and may adapt to the curvature of each recipient's bone/tissue structure. In some embodiments the free end of the wing does not contact the bone or tissue, but extends substantially towards the bone or tissue and may have a tapering portion or contour that adapts to the curvature of each recipient's bone/tissue structure.

An advantage of such a wing of the present invention may be to provide comfort to recipients regardless of where the medical device is implanted or how the medical device is implanted. The recipient using embodiments of the present invention may not notice or feel the protrusion caused by the medical device since the smooth transition makes the medical device less obvious to the touch. In addition, another advantage of the present invention is that the medical device may be placed in an excavation at any depth since the wing will flex outward. Another advantage of the present invention is that the smooth transition may reduce the chances of skin erosion around the medical implant device. Another advantage is that the smooth transition may reduce areas where body fluids may stagnate which could increase the likelihood of infection and/or biofilms forming on the device.

Figure 11A:
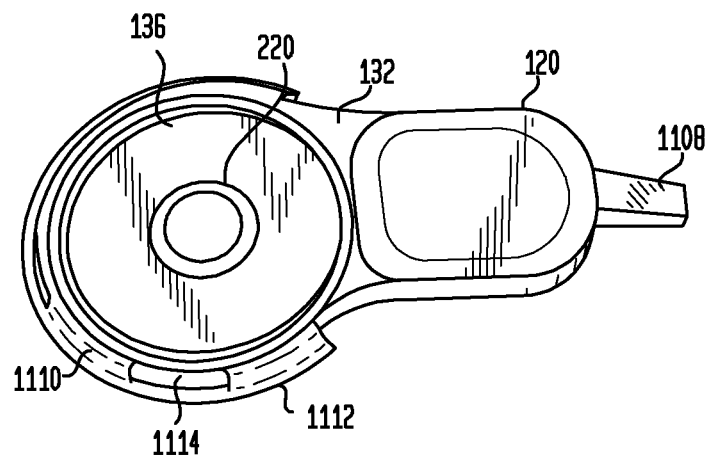
FIG. 11A is a perspective view of a flexible wing proximate to an internal coil of a malleable implantable medical device in accordance with an embodiment of the present invention.
Figure 11B:
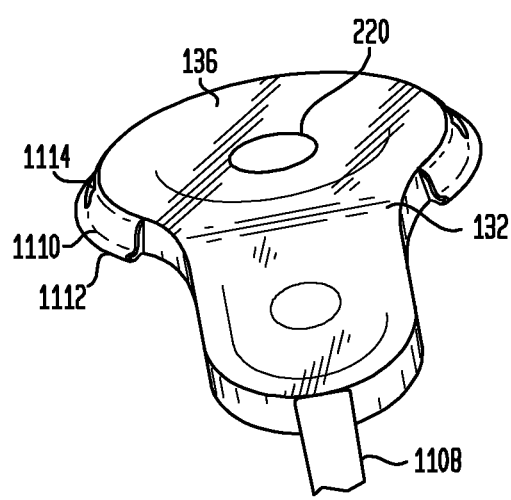
FIG. 11B is a perspective view of a flexible wing proximate to an internal coil of a malleable implantable medical device in accordance with an embodiment of the present invention.

FIGS. 11A and 11B are perspective top and end views respectively of a flexible wing proximate to an internal coil of a cochlear implant 100 in accordance with an embodiment of the present invention. Prosthetic hearing implant internal receiver unit 132 is depicted with internal coil 136 and stimulator unit 120. Stimulator unit 120 is connected to an electrode array 146 (not shown) through tab 1108. Wing 1110 may be provided on a portion of the perimeter or circumference of coil 136. Wing 1110 has a rim 1112, but may be constructed to have any other cross-sectional shape as described above. Wing 1110 may have several cuts 1114 where none of the sloping portion of wing 1110 is present. Rim 1112 extends along the length of cuts 1114 to form a continuous piece.

In an embodiment of the present invention, the wing may be provided without a rim, but still has several cuts in the wing. The cuts create several flaps of the wing that may flex independent of the other flaps. Alternatively, a rim may be positioned between two or more flaps to provide a uniform flexing amongst the flaps that are connected.

In an embodiment of the present invention, the wing may be provided without any cuts and may have a solid skirt shape as shown in and described in conjunction with FIG. 10D.

FIG. 12 shows a top perspective view of a prosthetic hearing implant internal receiver unit 132 having internal coil 136 and stimulator unit 120. Stimulator unit 120 is connected to an electrode array 146 (not shown) through tab 1108. Wing 1210 may be adhered to or placed on a portion of the perimeter or circumference of stimulator unit 120. Wing 1210 has a rim 1212, but may be constructed to have any other cross-sectional shape as described above. Wing 1210 may have several cuts 1214 where none of the sloping portion of wing 1210 is present. Rim 1212 and wing 1210 may extend around tab 1108.

FIGS. 13A and 13B show bottom perspective views of a prosthetic hearing implant internal receiver unit 132 having internal coil 136 and stimulator unit 120. Stimulator unit 120 is connected to an electrode array 146 through tab 1108. Wing 1310 may be adhered to or placed on the perimeter or circumference of implant internal receiver unit 132. Wing 1310 has a rim 1312, but may be constructed to have any other cross-sectional shape as described above. Wing 1310 may have several cuts 1314 where none of the sloping portion of wing 1310 is present. Rim 1312 and wing 1310 may extend around tab 1108.

Cuts 1114, 1214, 1314 in a wing 1110, 1210, 1310 of the present invention may provide fixation of internal receiver unit 132 by allowing tissue or bone to grow in the vacant area, such as what occurs in osseointegration. In addition, cuts 1114, 1214, 1314 may allow fluid circulation around internal receiver unit 132 to prevent bacterial growth.

Different wing shapes, such as shown in FIGS. 10A, 10B, 10C, 10D, and 10E, may be used on or in conjunction with internal receiver unit 132. In addition, one wing shape may be used on a portion of the housing for internal coil 136, while a second wing shape is used on the other portion of the housing. Alternatively, two or more wings may be used that have different wing shapes.

Figure 14A:
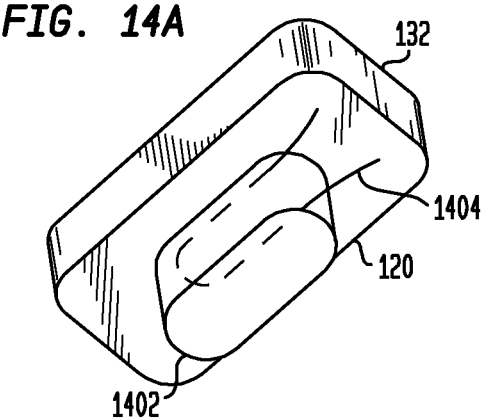
FIG. 14A is a perspective view of a removable pedestal proximate to a stimulator unit of a malleable implantable medical device in accordance with an embodiment of the present invention.

FIG. 14A is a perspective view of a removable pedestal 1402 proximate to a stimulator unit 120 of a cochlear implant 100 in accordance with an embodiment of the present invention. Other components of cochlear implant 100 such as internal coil 136 are not depicted in FIGS. 14A, 14B and 14C for purposes of simplicity and clarity. As depicted in FIG. 14A, removable pedestal 1402 is attached to a bottom surface of stimulator unit 120. A bottom surface is to be understood as the surface that of stimulator unit 120 which is facing approximately in the direction of the patient's bone or skull. Removable pedestal 1402 may be constructed of any suitable material, including the same flexible silicone material which may be used in one embodiment to form the biocompatible housing around stimulator unit 120 and internal coil 136.

Removable pedestal 1402 and receiver unit 132 may be manufactured and provided to the surgeon already joined to one another. A wire cutter 1404 is sandwiched between removable pedestal 1402 and a surface of internal receiver unit 132. Wire cutter 1404 is of sufficient length and positioned such that two ends of wire cutter 1404 extend beyond removable pedestal 1402 enough so that a tool or fingers may be used to grip and utilize the ends of wire cutter 1404 to either remove it from internal receiver unit 132 or as a cutting tool for cutting removable pedestal 1402, as will be described further below in conjunction with FIGS. 14B and 14C. Alternatively, removable pedestal 1402 may be manufactured separately from internal receiver unit 132 and provided for surgery as separate parts. When manufactured and provided as separate parts, these separate parts may be assembled and joined together a relatively short time before surgery by methods already known or later developed, such as by glue, screw, corresponding tabs or clips.

Figure 14B:
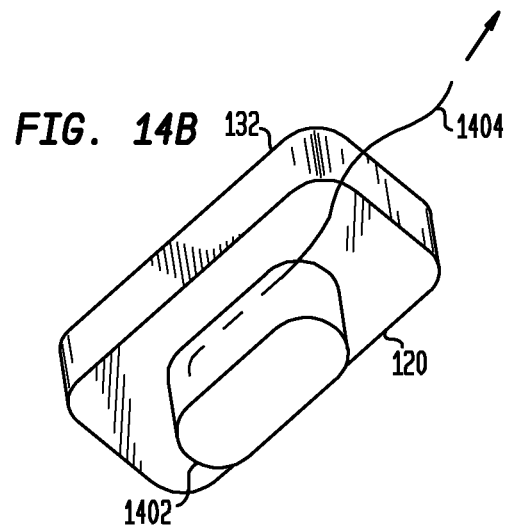
FIG. 14B is a perspective view of a removable pedestal proximate to a stimulator unit of a malleable implantable medical device in accordance with an embodiment of the present invention.

FIG. 14B is a perspective view of removable pedestal 1402 proximate to internal receiver unit 132 of a cochlear implant 100 in accordance with an embodiment of the present invention in which removable pedestal 1402 will remain affixed to internal receiver unit 132 after implantation. When removable pedestal 1402 and internal receiver unit 132 are provided to the surgeon as assembled or joined parts from the manufacturer, the surgeon has the option of altering internal receiver unit 132. The surgeon may do this to make it conform to the shape of the recipient's bone or skull depending on the condition and preparation of the implant site or through a preference for a surgical technique which avoids bone drilling. Where a suitably dimensioned bone bed has been formed in the bone through excavation, internal receiver unit 132 may be positioned in the implantation site with removable pedestal 1402 intact. Implanting internal receiver unit 132 with removable pedestal 1402 intact may be useful for maintaining the location of internal receiver unit 132, as any translational force on internal receiver unit 132 will be counteracted by the pedestal 1402 pushing against the adjacent surface of the bone bed. Furthermore, removable pedestal 1402 may be useful in maintaining the position of receiver unit 132 within a bone bed such that a desired distance between the bottom surface of receiver unit 132 and the surface of the excavated bone bed may be maintained. In this scenario, it may be desirable to remove wire cutter 1404 to minimize unnecessary objects being placed in the implantation site and to make removable pedestal 1402 a permanent part of the implanted receiver unit 132. To remove wire cutter 1404, a single end of wire cutter 1404 may be pulled which will remove wire cutter 1404 from the internal receiver unit 132 without cutting or otherwise detaching removal pedestal 1402 from internal receiver unit 132.

Figure 14C:
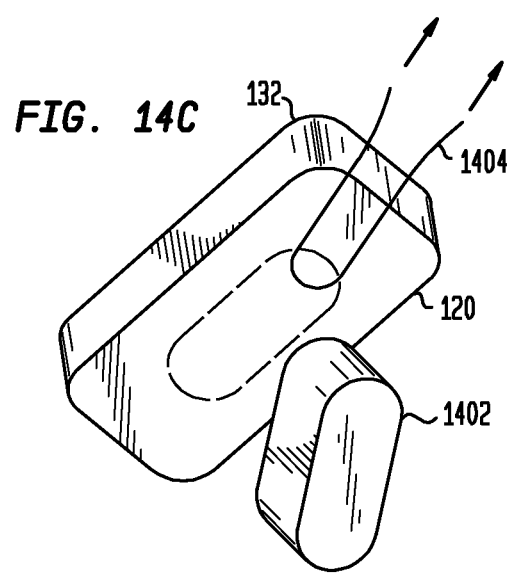
FIG. 14C is a perspective view of a removable pedestal proximate to a stimulator unit of a malleable implantable medical device in accordance with an embodiment of the present invention.

FIG. 14C is a perspective view of removable pedestal 1402 proximate to internal receiver unit 132 of a cochlear implant 100 in accordance with an embodiment of the present invention in which removable pedestal 1402 will be removed from internal receiver unit 132 prior to implantation. As discussed previously, when removable pedestal 1402 and internal receiver unit 132 are provided to the surgeon as assembled or joined parts from the manufacturer, the surgeon may opt to remove removable pedestal 1402 from internal receiver unit 132 in order to have internal receiver unit 132 conform to the shape of the recipient's bone or skull. For example, where the surgeon is not excavating a bone bed into which implantable components will be positioned, it may be desirable to modify internal receiver unit 132 to remove removable pedestal 1402 in order to minimize the thickness of internal receiver unit 132 or otherwise to have internal receiver unit 132 better conform to the shape of the recipient's bone or skull at the implantation site. To remove removable pedestal 1402 from internal receiver unit 132, both ends of wire cutter 1404 may be pulled simultaneously in order to cut or otherwise detach removable pedestal 1402. Other mechanisms for making removable pedestal 1402 easily removable from internal receiver unit 132 are also considered a part of this invention and may be provided or used together with, or instead of, wire cutter 1404. For example, a scalpel may be used to cut removable pedestal 1402 partially or completely from internal receiver unit 132. In another exemplary embodiment, removable pedestal 1402 may have a drastically reduced cross-section at a point on removable pedestal 1402 near internal receiver unit 132. The reduced cross-section may provide a weak point which can be torn by sufficient manual pulling force applied to the removable pedestal 1402 or to internal receiver unit 132. In a yet further exemplary embodiment, removable pedestal 1402 may have perforations along its border near internal receiver unit 132 which are configured to tear when sufficient manual pulling force is applied to removable pedestal 1402 or to internal receiver unit 132.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

The invention claimed is:

1. An apparatus comprising:
   a hermetic enclosure;
   an elastomer encasing the hermetic enclosure,
   wherein the elastomer forms a pedestal extending from a first side of the apparatus; and
   wherein the pedestal is configured to be separated from the elastomer.

2. The apparatus of claim 1, wherein the pedestal is integral with the elastomer.

3. The apparatus of claim 2, wherein the pedestal and the elastomer comprise silicone.

4. The apparatus of claim 1, wherein the pedestal is substantially rectangular.

5. The apparatus of claim 1, wherein the first side comprises a surface of the apparatus that, when implanted, faces a skull.

6. The apparatus of claim 1, wherein the pedestal includes perforations that are configured to tear when sufficient manual pulling force is applied, thereby making the pedestal configured to be separated from the elastomer.

7. An auditory prosthesis comprising:
   a receiver coil;
   a stimulator unit electrically connected to the receiver coil;
   an elastomer housing surrounding both the receiver coil and the stimulator unit, and
   a pedestal extending from a surface of the elastomer housing.

8. The auditory prosthesis of claim 7, wherein the pedestal is disposed proximate the stimulator unit and distal from the receiver coil.

9. The auditory prosthesis of claim 7, wherein the stimulator unit is contained within the elastomer housing but not within the pedestal, such that the pedestal can be disconnected from the elastomer housing.

10. The auditory prosthesis of claim 7, wherein the surface is a bottom surface of the elastomer housing.

11. The auditory prosthesis of claim 10, wherein the pedestal is silicone formed integrally with the elastomer housing.

12. The auditory prosthesis of claim 7, wherein the pedestal has a reduced cross-section on at least one location on the pedestal.

13. The auditory prosthesis of claim 7, wherein the pedestal is rectangular.

14. The auditory prosthesis of claim 7, wherein the stimulator unit is disposed in a hermetic enclosure.

15. A method of implanting into a recipient an auditory prosthesis having a stimulator unit and a silicone housing surrounding the stimulator unit, the method comprising:
   forming a bone bed in a skull of the recipient; and
   inserting a portion of the silicone housing into the bone bed, without inserting the stimulator unit into the bone bed.

16. The method of claim 15, wherein the portion of the silicone housing is rectangular and the bone bed comprises a shape corresponding to the portion of the silicone housing.

17. The method of claim 15, wherein the portion of the silicone housing extends from an underside of the silicone housing, wherein the underside of the silicone housing contacts the skull when the portion of the silicone housing is inserted into the bone bed.

18. The method of claim 17, wherein the underside of the silicone housing conforms to the skull of the recipient when the portion of the silicone housing is inserted into the bone bed.

19. The method of claim 15, wherein the stimulator unit does not extend below a surface of the skull when the portion of the silicone housing is inserted into the bone bed.

20. The method of claim 15, wherein the stimulator unit is disposed in a hermetic enclosure.

* * * * *